United States Patent [19]
Merrill et al.

[11] Patent Number: 5,900,518
[45] Date of Patent: May 4, 1999

[54] HEAT INTEGRATION IN ALKYLATION/TRANSALKYLATION PROCESS

[75] Inventors: James T. Merrill, Katy, Tex.; Joseph Honn Tudor, Baton Rouge, La.

[73] Assignee: Fina Technology, Inc., Dallas, Tex.

[21] Appl. No.: 08/739,897

[22] Filed: Oct. 30, 1996

[51] Int. Cl.⁶ .................................. C07C 2/64; C07C 2/00
[52] U.S. Cl. ..................... 585/323; 585/449; 585/450; 585/467; 585/470; 585/475; 585/446
[58] Field of Search ................................... 585/323, 449, 585/450, 467, 470, 475, 446

[56] References Cited

U.S. PATENT DOCUMENTS

| | | | |
|---|---|---|---|
| 4,107,224 | 8/1978 | Dwyer | 260/671 R |
| 4,185,040 | 1/1980 | Ward et al. | 585/467 |
| 4,774,377 | 9/1988 | Barger et al. | 585/323 |
| 4,885,424 | 12/1989 | Ferk et al. | 585/450 |
| 4,922,053 | 5/1990 | Waguespack et al. | 585/449 |
| 5,336,821 | 8/1994 | DeGraff et al. | 585/402 |

FOREIGN PATENT DOCUMENTS

467007  1/1992  European Pat. Off. .

*Primary Examiner*—Hien Tran
*Assistant Examiner*—Thuan D. Dang
*Attorney, Agent, or Firm*—William D. Jackson; Pamela S. Smith; M. Norwood Cheairs

[57] ABSTRACT

The present invention addresses heat integration in an alkylation/transalkylation process involving alkylation of an aromatic substrate with a $C_2$–$C_4$ alklating agent coupled with separation to recover a monoalkylated aromatic product and liquid phase transalkylation of a polyalkylated product. Aromatic feedstock and a $C_2$–$C_4$ alkylating agent are supplied to an alkylation reaction zone which is operated to produce an alkylated product. The output from the alkylation reaction zone initially travels through an arrangement of heat exchangers. From there, the alkylation effluent passes into the first separation zone which is operated to produce a lower boiling fraction comprising the aromatic substrate, which may be recycled to the alkylation reaction zone, and a higher boiling fraction comprising a mixture of monoalkylated and polyalkylated aromatics. This lower boiling fraction first travels back through portions of the heat exchanger arrangement on the way to recycle into the alkylation zone. The higher boiling fraction of the first separation zone is supplied to a secondary separation zone to produce a second lower boiling fraction comprising the desired monoalkylated product and a higher boiling fraction comprising polyalkylated product. At least a portion of the higher boiling polyalkylated fraction passes through a portion of the heat exchanger arrangement into a transalkylation reaction zone containing a molecular sieve transalkylation catalyst operated under liquid phase conditions to cause disproportionation of the polyalkylated fraction to arrive at a disproportionation product having a reduced polyalkylated aromatic content and an enhanced monoalkylated aromatic content.

31 Claims, 3 Drawing Sheets

HEAT INTEGRATION IN ALKYLATION/TRANSALKYLATION PROCESS

FIELD OF THE INVENTION

This invention relates to the transalkylation of polyalkylated aromatic compounds and more particularly to an alkylation/transalkylation process involving alkylation of a benzene feed stock with a $C_2$–$C_4$ alkylating agent and liquid phase transalkylation of resulting polyalkyl benzenes, treatment of the alkylation product in a separation zone, recycle of at least a portion of the transalkylation product to the separation zone, and the processes for heating and exchanging heat between different streams in the overall process.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly-alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene.

Another example involving the ethylation of benzene under vapor phase reaction conditions coupled with the recycle of polyethylbenzene containing products back to the alkylation reactor is disclosed in U.S. Pat. No. 4,922,053 to Waguespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of the total diethylbenzene feed to the column. The diethylbenzene overheads fraction is recycled to the alkylation reactor while a side cut containing the remaining diethylbenzene and triethylbenzene and higher molecular weight compounds is supplied to the rector along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-β, zeolite-Y or zeolite-Ω or in the vapor phase employing a catalyst such as silicate or ZSM-5. in the Butler process where vapor phase alkylation is followed by liquid phase transalkylation, substantial quantities of water may be included in the feedstream to the alkylation reactor. In this case, the feed to the transalkylation reactor may be dehydrated to lower the water content.

SUMMARY OF THE INVENTION

In accordance with the present invention there is provided an alkylation/transalkylation process involving alkylation of an aromatic substrate with a $C_2$–$C_4$ alkylating agent coupled with separation to recover a monoalkylated aromatic product and liquid phase transalkylation of a polyalkylated product. In a preferred embodiment of the invention, a benzene feedstock and a $C_2$–$C_4$ akylating agent are supplied to an alkylation reaction zone containing a plurality of serially connected catalyst beds operating at different temperatures which is operated to produce an alkylated product comprising a mixture of monoalkyl and polyalkyl benzenes. In this embodiment of the invention the alkylation zone is operated under gaseous phase conditions. The output from the alkylation reaction zone is supplied to a first separation zone, which in the primary embodiment serves as a benzene recovery zone, which is operated to produce a lower boiling fraction comprising the aromatic substrate, which may be recycled to the alkylation reaction zone, and a higher boiling fraction comprising a mixture of monoalkylated and polyalkylated aromatics. The higher boiling fraction is supplied to a secondary separation zone to produce a second lower boiling fraction comprising the desired monoalkylated product and a higher boiling fraction comprising polyalkylated product.

At least a portion of the polyalkylated fraction including substantially dialkylated and trialkylated aromatics supplied, along with the aromatic substrate, to a transalkylation reaction zone containing a molecular sieve transalkylation catalyst. The transalkylation zone is operated under liquid phase conditions to cause disproportionation of the polyalkylated fraction to arrive at a disproportionation product having a reduced polyalkylated aromatic content and an enhanced monoalkylated aromatic content. At least a portion of the disproportionation product is supplied to the benzene recovery zone. The transalkylation reaction zone is operated at a average temperature below the average temperature of the alkylation reaction zone and under conditions to maintain the benzene in the liquid phase. In a specific application of this embodiment of the invention to a procedure employing gas-phase ethylation of benzene followed by liquid phase transalkylation, the average temperature of the transalkylation reaction zone is at least 100° C. less than the average temperature of the alkylation reaction zone.

In the primary embodiment of the invention when the output from the alkylation reaction zone is supplied to the benzene recovery zone it is first passed through three heat exchangers. It initially travels in parallel through one pair of heat exchangers, a first heat exchanger and a second heat exchanger, and then follows through a third exchanger in series with the two parallel heat exchangers. From there, the alkylation effluent passes into the benzene recovery zone.

As discussed, the benzene recovery zone separates off a lower boiling fraction comprising the aromatic substrate which is then recycled to the alkylation reaction zone. Before going to the alkylation reaction zone, this lower boiling point fraction first travels through the third heat exchanger where it comes in indirect contact with the alkylation effluent from the initial alkylation reaction. The lower boiling point fraction then travels through the first heat exchanger where again it comes into indirect contact with the alkylation effluent from the initial alkylation reaction. In one embodiment, the lower boiling point fraction finally passes through a reactor feed heater before reaching the alkylation zone. In the preferred embodiment some portion of the lower boiling point fraction is separated from the main group before travelling through the heat exchangers and instead travels directly to an alternate path within the same rector feed heater, after which point it joins the remaining portion of the lower boiling point fraction which has passed through both heat exchangers and the heater. The joined streams then travel to the alkylation zone.

In yet another aspect of this invention, the portion of the polyalkylated fraction including substantially all dialkylated and trialkylated aromatics while being supplied to the transalkylation reaction zone passes through the second heat exchanger discussed previously. In this heat exchanger it comes into indirect contact with the alkylation effluent from the initial reaction in the alkylation zone. From this point it travels into the transalkylation zone.

The primary embodiment serves to optimize the use of thermal energy in the process. Its effect compared with the pre-existing arrangement has been to lower the temperatures throughout the process, maintain constant temperature output, and to heat the transalkylation feed with little new equipment. The primary embodiment also eliminates the need for a flash vessel.

In an alternative embodiment a flash vessel is used to replace the need for the parallel heat exchanger arrangement between the alkylation zone and first separation zone. In this alternative embodiment, the effluent from the alkylation zone travels serially through all three heat exchangers before entering the benzene recovery zone. The recycled benzene taken from the overhead portions in the benzene recovery zone travels through only one heat exchanger in indirect contact with the alkylation effluent. The transalkylation feed from the secondary separation zone travels through one heat exchanger in indirect contact with the alkylation effluent. And, the transalkylation effluent (or disproportionation product) travels through the third heat exchanger in indirect contact with the alkylation effluent. The disproportionation product is then sent to the flash vessel, where the aromatic component is separated from the ethylbenzene and polyethylbenzenes, and both fractions are sent to sites in the benzene recovery zone.

The use of the flash vessel instead of the parallel heat exchanger configuration may be preferable in some retrofit applications where the heat exchanger configuration is not available or if a flash vessel is already in place. It also serves the same goals as the primary embodiment of overall lowering of temperatures, maintaining constant temperature output, and heating the transalkylation feed.

A third embodiment, also for use in some retrofit applications, involves the use of only two heat exchangers connected serially with respect to the alkylation effluent. In this embodiment, the lower boiling fraction from the benzene recovery zone passes to the alkylation reactor either directly or by way of the reactor feed heater, in either event without passing through a heat exchanger in relation ship with the alkylation effluent. This arrangement still serves the same goals of overall lowering of temperatures, maintaining constant temperature output, and heating the transalkylation feed.

All of these embodiments may also take advantage of a line in the reactor feed heater, which has become unused due to other process changes, to heat some portion of the recycled benzene.

DETAILED DESCRIPTION OF THE INVENTION

The preferred application of the invention can be carried out employing gas-phase alkylation coupled with liquid phase transalkylation and appropriate recycle of the transalkylated product to a separation zone.

In its more general aspects, the invention involves transalkylation coupled with aromatic alkylation employing $C_2$–$C_4$ alkylating agent which, broadly stated, can be alkylating agents such as olefins, alkanes, alkohalides, alcohols, ethers, and esters. The most widely used alkylating agents are ethylene and propylene applied in the production of ethylbenzene and cumene, respectively. The invention is specially applicable to the ethylation of benzene under conditions in a manner in which by-product xylene yields are reduced. The invention will be described specifically by reference to the production of ethylbenzene together with the attendant transalkylation of polyethylbenzenes. More specifically, the invention is applicable to integration and optimization of the thermal interactions in an alkylation/transalkylation process for production of ethylbenzenes.

A conventional process for the production of ethylbenzene involves recycling polyethylbenzenes, separated from the ethylbenzene product, to the alkylation reactor where they undergo transalkylation to yield ethylbenzene. A by-product of this procedure is increased xylene yield in the effluent from the alkylation reactor. The presence of xylenes complicates downstream processing in separate steps. A particular impact of a significant xylene content in the product stream is that it often mandates operation of the distillation column from which the ethylbenzene is taken overhead in a manner to provide a substantial ethylbenzene content, often times 15 to 20% or more, in the bottom polyethylbenzene fraction. For example, ethylbenzene produced in accordance with the present invention can be employed in the production of styrene by catalytic dehydrogenation. The boiling points of ortho-xylene and styrene are very close, within 1° C. of one another. As a practical matter, the ethylbenzene specifications will call for a very low xylene content, normally less than 2,000 ppm. In order to meet this specification, it is normally necessary to operate the ethylbenzene column under moderate distillation conditions resulting in a high ethylbenzene content in the bottoms fraction as described above. The present invention, by carrying out polyethylbenzene transalkylation in a separate reactor under relatively mild liquid phase conditions, minimizes the xylene make in the manufacturing process. This enables ethylbenzene recirculation to be reduced by limiting the ethylbenzene content in the polyethylbenzene fraction to 5 wt. % or less and, where preferred catalysts are used to further minimize xylene make, down to about 2 wt. % or less ethylbenzene.

A preferred aspect of the present invention involves supplying the polyethylbenzene fraction, including both diethylbenzene and triethylbenzene in higher weight molecular compounds to the transalkylation reactor as contrasted with separating out a substantial portion of diethylbenzene for recycle to the alkylation zone or separating out trialkyl aromatics with transalkylation only if dialkylbenzene. In this respect, depending upon the configuration of the interface of the transalkylation reactor and polyethylbenzene or other separation zones, substantially all of the diethylbenzene and some or a significant portion of the triethylbenzene content will be supplied to the transalkylation reactor. In either case, the practical effect of this embodiment of the invention is that recycled to the alkylation reactor is limited to benzene and lighter components, e.g., ethylene, while most, if not all of the triethylbenzenes together with diethylbenzenes are retained in the system ultimately for conversion to benzene and ethylbenzene. This offers significant advantages over the prior art process, not only in terms of reduced to xylene make as described previously, but also in terms of ultimate product yield.

The present invention modifies the heat transfer systems in the process to optimize the use of thermal energy. In the previous process without a transalkylation step, there were two heat exchangers serially aligned with respect to the alkylation effluent while aligned in parallel with respect to recycled benzene. These two heat exchangers were used to exchange heat between the recycled benzene and the alkylation effluent. The preferred embodiment of the present invention adds a third heat exchanger placed in parallel with respect to the alkylation effluent with one of the two previous heat exchangers. The transalkylation feed is also passed through the new heat exchanger in indirect contact with the alkylation effluent. Neither of these activities were present in the pre-existing system. The overall effect is to lower the temperatures throughout the process, maintain constant temperature output and to heat the transalkylation feed with little new equipment.

The alternative embodiment of the current invention adds a flash vessel in addition to the third heat exchanger. The flash vessel serves to separate the benzene from the ethylbenzenes and polyethylbenzenes in the disproportionation product in order to provide a good ratios in the benzene recovery zones as needed. Additionally, prior to reaching the flash vessel, the disproportionation product is passed through one of the heat exchangers in substitution of one of the recycled benzene trips through a heat exchanger. The alternative embodiment also assists in providing lowered temperatures, a constant temperature output, and heat to the transalkylation feed, as well as improved control of the benzene to alkylated benzene ratios in the benzene recovery stages.

Finally, another aspect of both embodiments of the current invention is the use of a spare coil in a reactor feed heater, opened up by the other process changes taking place. In both embodiments, some of the recycled benzene may be diverted around the heat exchangers and through the spare coil before being merged back into the recycled benzene stream. This diversion makes efficient use of the available heat and equipment present in the process.

Figure 1:
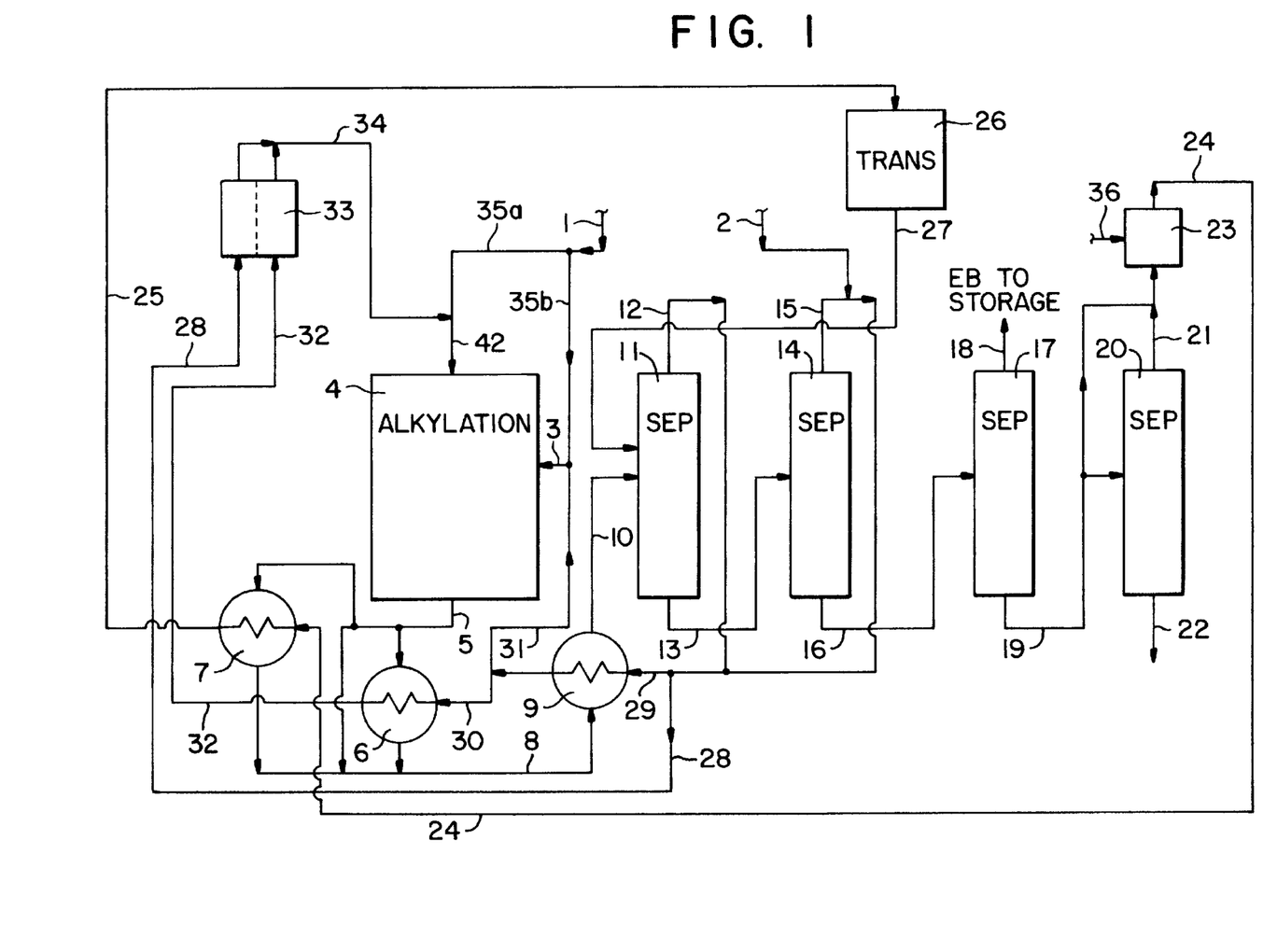
FIG. 1 is a simplified schematic flow diagram illustrating one embodiment of the invention in which two parallel heat exchangers followed by one serial heat exchanger are used between the alkylation zone and the first separation zone.
Figure 2:
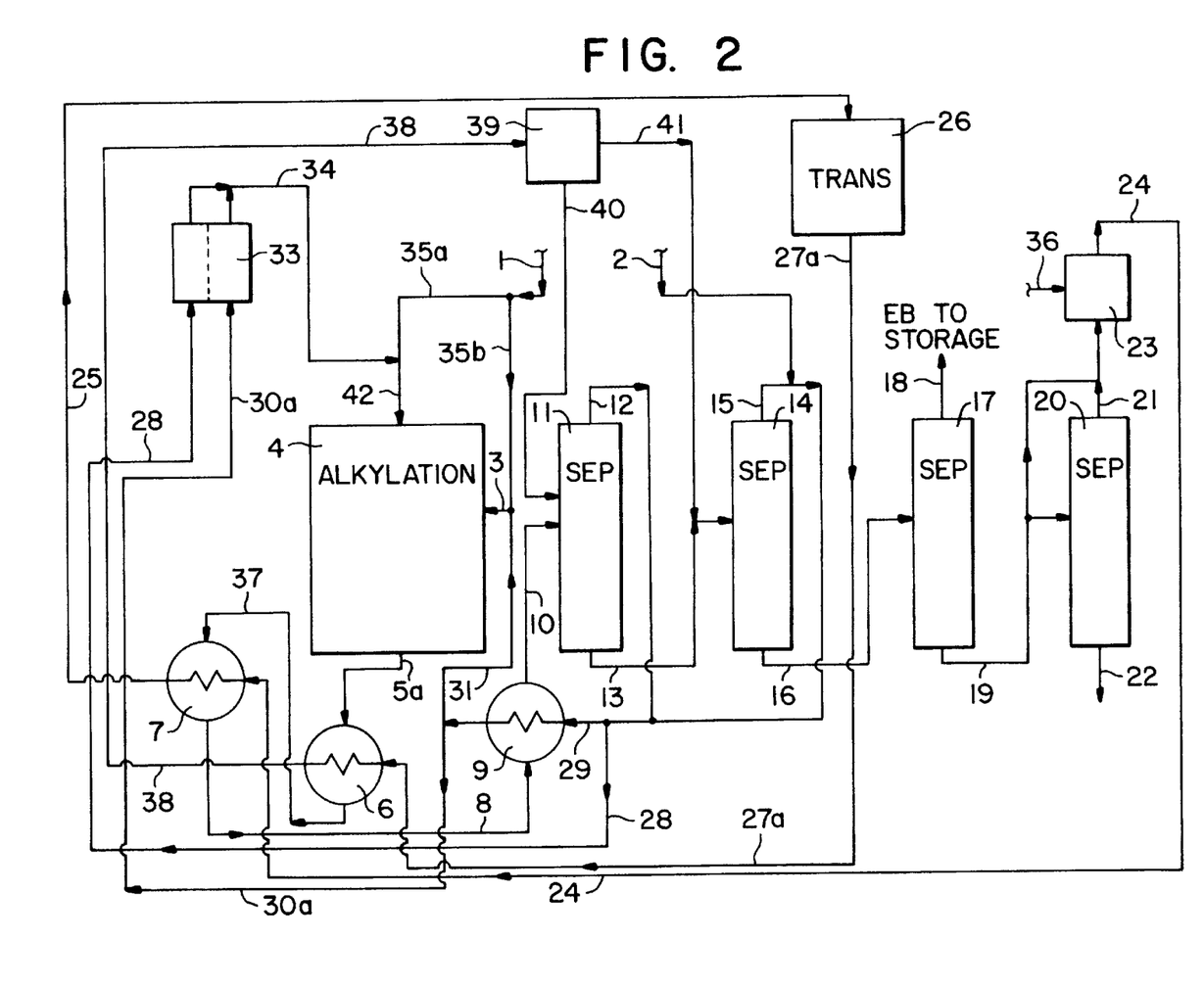
FIG. 2 is a schematic illustration of a modification of the process of FIG. 1 in which the parallel arrangement of heat exchangers following the alkylation zone is replaced by the use of a flash vessel.

With reference to the drawings, FIG. 1 through 2 illustrate schematic flow diagrams illustrating different embodiments of the invention. It will be assumed for purposes of discussion that the invention is applied in the production of ethylbenzene by reaction of ethylene with benzene and that the alkylation reaction is carried out as a gas-phase reaction employing a catalyst such as silicate or ZSM-5, while the transalkylation reaction using a zeolite catalyst is carried out under temperature and pressure conditions to maintain the benzene in the liquid phase and effective to cause disproportionation of the polyalkylated benzene to arrive at a disproportionation product having a reduced polyalkyl benzene content and an enhanced monoalkyl benzene content. Various embodiments and additional detail on the catalytic and process requirements and methods involved in the present invention are incorporated into the alkylation/transalkylation process as described in co-pending Application Ser. No. 08/739,564 filed of even date herewith by James Merrill et al, entitled "Gas Phase Alkylation-Liquid Transalkylation Process" and further identified by attorney docket number FINT B8152, which disclosure is incorporated herein by reference.

Returning to the heat integration aspects which are the focus of this application, referring first to FIG. 1, a feed stream 35a containing ethylene supplied via line 1 and a benzene rich stream 34 is passed first to an alkylation reaction zone 4. The alkylation reactor which may comprise a plurality of serially connected catalyst beds operated at different temperatures (which in one embodiment are progressively increasing temperatures) and with interphase injection of ethylene and benzene, normally is operated to maintain the benzene in gaseous phase. In the preferred embodiment the alkylation reaction zone consists of a pair of the described reactors such that both reactors may be active or one reactor may be active while the other is diverted out of the process loop undergoing catalyst regeneration. Stream 3, which derives from the combination of stream 35b and stream 31 may be supplied to stages or catalyst beds following the initial stage of the alkylation reactor for injection of ethylene and benzene.

The effluent stream 5 from the alkylation reactor stream is divided such that a portion travels to each of two heat exchangers while a third portion may bypass both of the two heat exchangers, a first heat exchanger 6 and a second heat exchanger 7, which are mounted in parallel with one another with respect to stream 5. In heat exchangers 6 and 7 the effluent stream is placed in indirect contact with a recycled benzene stream 30 (which constitutes a portion of recycled benzene stream 29) and the transalkylation feed stream 24 respectively. The indirect contact in heat exchangers 6 and 7 will provide a heat exchange relationship in which the divided alkylation effluent stream 5 will give up heat to the recycled benzene stream 30 and the transalkylation feed stream 24 respectively. Upon leaving these two heat exchangers the alkylated product streams merge back together with each other and with the stream which bypassed the two heat exchangers into a common stream 8 which then travels through heat exchanger 9. In heat exchanger 9 the stream 8 comes into indirect contact with a recycled benzene stream 29. The indirect contact in heat exchanger 9 will provide a heat exchange relationship, with the entirety of the alkylation reactor effluent, remerged in stream 8, giving up heat to the recycled benzene stream 29. The remerged alkylation effluent stream 8 leaves heat exchanger 9 as stream 10 and travels to the benzene recovery zone which in the embodiment illustrated comprises a multistage fractionation system.

Initially, stream 10 enters a prefractionation column 11, the first stage of the benzene recovery zone, which is operated to provide a light overheads fraction including benzene which is withdrawn and recycled to the alkylation reactor as stream 12. The prefractionation column 11 also produces a heavier liquids fraction containing benzene, ethylbenzene, and polyethylbenzenes.

This output of the heavier fraction from the prefractionation column in the benzene recovery zone is supplied via of stream 13 to a fractionation or benzene separation column 14 which constitutes the second stage in the benzene recovery zone. Column 14 produces an overhead fraction which contains benzene, which is recycled via stream 15 to the alkylation reactor, and a heavier bottoms fraction. The heavier bottoms fraction from fractionation column 16 is supplied via stream 16 to an ethylbenzene separation zone or the secondary separation zone.

In the embodiment of FIG. 1 this secondary separation zone takes the part of two additional columns 17 and 20. The heavier bottoms fraction from fractionation column 14 is supplied to the ethylbenzene separation column 17. The overheads fraction from ethylbenzene separation column 17, of course, comprises ethylbenzene which is supplied in the form of stream 18 to storage or to any suitable product destination. By way of example, the ethylbenzene may be used as a feed stream to a styrene plant in which styrene is produced by the dehydrogenation of ethylbenzene.

The bottoms fraction of ethylbenzene separation column 17 containing polyethylbenzenes, heavier aromatics, and preferably only a small amount of ethylbenzene, is supplied via stream 19 to a second column in the secondary separation zone which serves as a polyethylbenzene separation column 20. The bottoms fraction of column 20 comprises a residue in the form of stream 22.

The overhead fraction from polyethylbenzene separation column 20 comprising polyethylbenzenes, including diethylbenzene and triethylbenzene (usually in relatively small quantities), and a minor amount of ethylbenzene is supplied through stream 21 to a transalkylation surge drum 23. In the preferred embodiment, some portion of stream 19 may bypass the polyethylbenzene separation column to merge with stream 21 in transit to the transalkylation surge drum 23. Also supplied to the transalkylation surge drum is a stream of benzene from elsewhere in the process by way of stream 36. By minimizing the amount of ethylbenzene recovered from the bottom of ethylbenzene separation column 17, the ethylbenzene content of the transalkylation feed stream is kept small in order to drive the transalkylation reaction in the direction of ethylbenzene production.

The polyethylbenzene fraction withdrawn overhead in the means of stream 21 is mixed with benzene (which may be recycled from elsewhere in the process) provided by stream 36 and then the resulting transalkylation feed stream 24 is supplied to the second heat exchanger 7. While travelling through the second heat exchanger 7, the transalkylation feed stream 24 is placed in indirect contact with the alkylation effluent stream 37. This indirect contact in heat exchanger 7 results in a heat exchange relationship, with the entirety of the alkylation effluent via stream 37 giving up heat to the transalkylation feed stream 24. From this point the transalkylation feed stream leaves as stream 25 and is supplied to the transalkylation zone 26. In the preferred embodiment the transalkylation reaction zone consists of a pair of transalkylation reactors such that both reactors may be active or that one reactor may be active while the other is diverted out of the process loop undergoing catalyst regeneration. The output from the transalkylation zone, containing benzene, increased amounts of ethylbenzene, and diminished amounts of polyethylbenzenes, is supplied by stream 27 to the benzene recovery zone. In the preferred embodiment, the stream 27 is specifically supplied to the first stage of the benzene recovery zone, prefractionation column 11.

In the embodiment described in FIG. 1, the benzene is recycled through the combination of streams 12 and 15, the overhead fractions of separator columns 11 and 14 in the benzene recovery zone, additional "fresh" benzene may also be introduced from line 2 resulting in a combined stream comprising the material of streams 12 and 15 and line 2. This combined stream is then separated into streams 28 and 29. Stream 29 travels through the third heat exchanger 9 where it comes into indirect contact with the alkylation effluent as it moves from stream 8 into stream 10. This indirect contact in heat exchanger 9 yields a heat exchange relationship, with the entire alkylation effluent, remerged in stream 8, giving up heat to the recycled benzene stream 29. After travelling through heat exchanger 9 the recycled benzene is separated into streams 30 and 31. Stream 30 enters the first heat exchanger 6 where it comes into indirect contact with the alkylation effluent stream as it moves from stream 5 to stream 8. Stream 31, by comparison, is combined with stream 35b into stream 3 which may be injected into the beds following the initial catalyst bed in the alkylation zone.

Stream 30, after passing through the first heat exchanger 6, emerges as stream 32 of recycled benzene which is then sent to the reactor feed heater 33. Stream 2 travels directly to the reactor feed heater 33, without passing through the heat exchangers 9 and 6. Stream 32 passes through a coil of the reactor feed heater 33 and emerges on the other side to be combined with the emerging stream 28 into stream 34. Stream 28 passes through a separate coil in reactor feed heater 33 and emerges from reactor feed heater 33 to be combined into stream 34. Stream 34 combines with stream 35a to form stream 42 which enters as the ethylene and benzene component sent into the initial stage of the alkylation zone.

The embodiment of FIG. 1 may be modified by eliminating bypass stream 28 and recycling the benzene through the third and first heat exchangers, 9 and 6 respectively, and through the reactor feed heater 33. Thus there is no usage of recycled benzene in the spare coil in reactor feed heater 33. However, in the preferred embodiment of the invention, each heat exchanger 6, 7, & 9 will also be accompanied by a bypass for each of the streams traveling through it (not illustrated) in order to provide better control of the resulting temperature of the streams after the respective heat exchangers.

FIG. 2 illustrates another embodiment of the invention in which like components are indicated same reference numerals as used in FIG. 2. The alternative embodiment shown in FIG. 2 involves several differences in configuration associated with a flash vessel 39. In FIG. 2, instead of being arranged in the parallel configuration of FIG. 1, first and second heat exchangers 6 and 7 respectively, are in series with respect to alkylation effluent stream 5a and are followed up by third heat exchanger 9 also in series with respect to alkylation effluent stream 5a. Thus, alkylation effluent stream 5a travels first through first heat exchanger 6. Then it travels out of heat exchanger 6 via stream 37 to enter second heat exchanger 7. Then it travels out of heat exchanger 7 via stream 8 to third heat exchanger 9 and then on into the benzene recovery zone.

Further in the embodiment of FIG. 2, the effluent from the transalkylation zone 26 passes in stream 27a through first heat exchanger 6 in indirect contact with the effluent from the alkylation zone via stream 5a (said alkylation effluent then passing through heat exchangers 7 and 9). This indirect contact in heat exchanger 6 provides a heat exchange relationship, with the entire alkylation effluent via stream 5a giving up heat to the transalkylation effluent stream 27a. Upon leaving heat exchanger 6, the effluent from the transalkylation zone then travels via stream 38 to a flash vessel 39. The flash vessel operation involves a reduction in pressure to separate out a benzene rich phase, which is withdrawn via stream 40, from the remaining heavier fraction which leaves via stream 41. Stream 40 is then supplied to the first stage of the benzene recovery zone, prefractionation column 11. The stream 41 is supplied to the second stage of the benzene recovery zone, fractionation column 14, where it mixes with the bottoms fraction from prefractionation column 11. In an alternative embodiment not shown, in a prefractionation column 11 with multiple beds, trays, stages or a packed column, stream 40 is to be supplied to the initial bed or one of the earlier beds in prefractionation column 11, while the stream 41 of ethylbenzenes and polyethylbenzenes is also supplied to the prefractionation column 11 to an intermediate or later bed.

Also, it may be noted that the recycled benzene in streams 12 and 15 (plus the "fresh" benzene from line 2) may still be divided into streams 28 and 29, with stream 29 travelling through heat exchanger 9. Upon leaving heat exchanger 9 the recycled benzene again is split into stream 31, which travels to the following catalyst beds in the alkylation zone, and stream 30a. Stream 30a however goes directly from third heat exchanger 9 to the reactor feed heater 33, by-passing first heat exchanger 6 (unlike the embodiment of FIG. 1 in which the recycled benzene output of heat exchanger 9 is supplied to heat exchanger 6). Stream 28 meanwhile by-passes the heat exchanger 6 and travels to the alternate or spare coil in the reactor feed heater 33 before merging with the stream 30a out of reactor feed heater 33 into combined stream 34. Similarly, as described above with reference to FIG. 1, an alternative embodiment would have no stream 28 and would not use the spare coil in the reactor feed heater 33 to heat recycled benzene.

Figure 3:
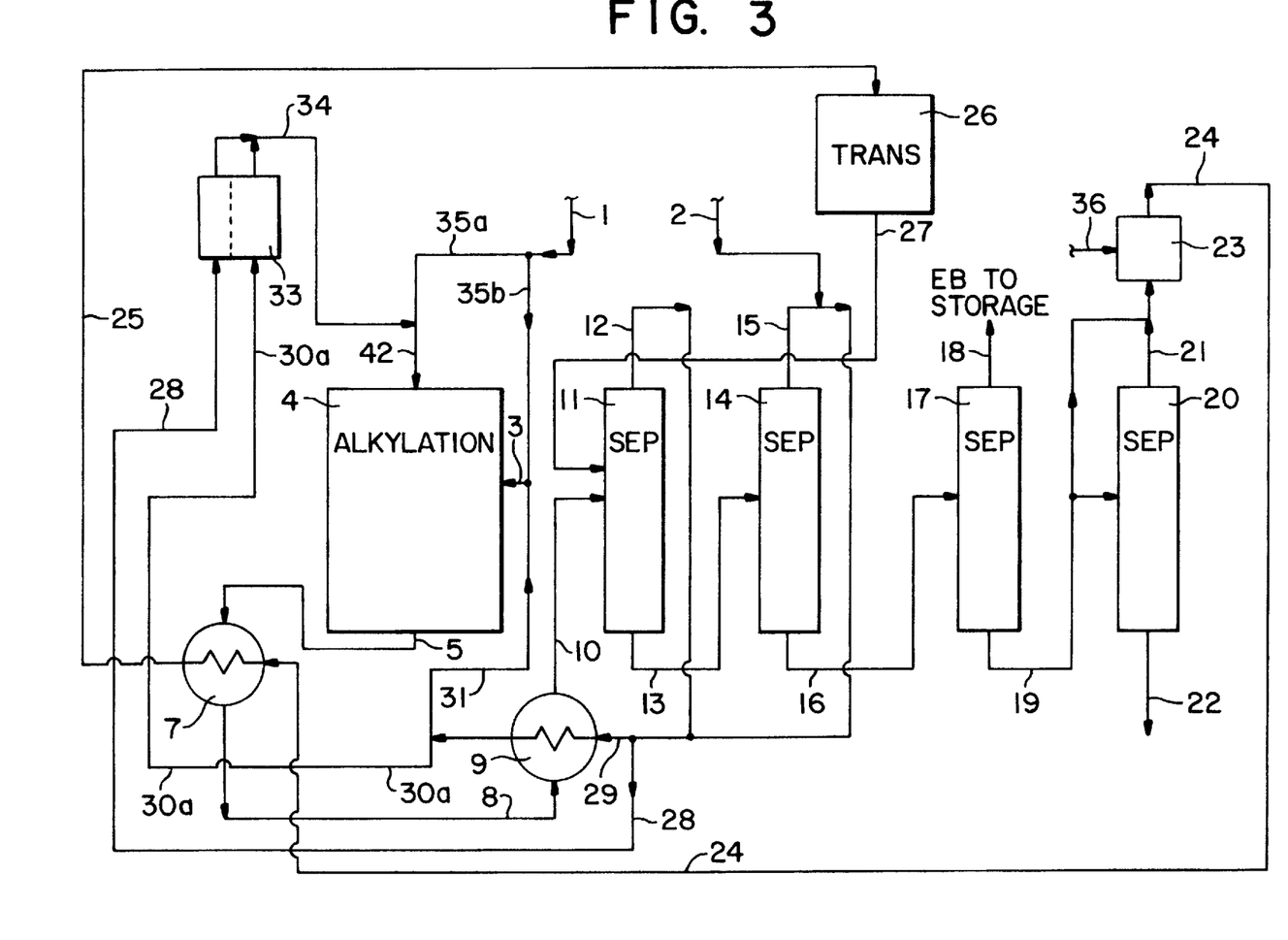
FIG. 3 is a schematic illustration of a modification of the process of FIG. 1 in which only two heat exchangers are used following the alkylation zone.

FIG. 3 illustrates a third embodiment of this invention in which uses only two heat exchangers 7 & 9. The key difference in FIG. 3 is the absence of heat exchanger 6. This results in two changes in flow patterns from FIG. 1. Alkylation effluent stream 5 now travels directly to one heat exchanger 7 emerges as stream 8 and then serially travels through another heat exchanger 9. As previously discussed with respect to all heat exchangers, it is preferred that by-passes are present (not illustrated) allowing some portion, all, or none of stream 5 to by-pass heat exchanger 7 and some portion, all, or none of stream 8 to by-pass heat exchanger 9.

The other difference in flow pattern from the embodiment illustrated in FIG. 1 is that like FIG. 2, upon leaving heat exchanger 9 the recycled benzene again is split into stream 31, which travels to the following catalyst beds in the alkylation zone, and stream 30a, which goes directly from heat exchanger 9 to the reactor feed heater 33 without passing through another heat exchanger.

Having described specific embodiments of the present invention, it will be understood that modification thereof may be suggested to those skilled in the art, and it is intended to cover all such modifications as fall within the scope of the appended claims.

What is claimed:

1. In an alkylation/transalkylation process, the steps comprising:

a) supplying a feedstock containing benzene to a multi-stage alkylation reaction zone having a plurality of series connected catalyst beds which are operated at different temperatures;

b) supplying a $C_2$–$C_4$ alkylating agent to said reaction zone;

c) operating said reaction zone at temperature and pressure conditions to maintain said benzene in the gaseous phase and cause gas-phase alkylation of said benzene by said alkylating agent in said catalyst beds to produce an alkylated product comprising alkyl benzene and polyalkyl benzene;

d) recovering said alkylated product from said reaction zone and supplying a first portion of said product from said reaction zone sequentially through first and second heat exchangers to a benzene recovery zone for the separation of benzene from alkylation product;

e) operating said benzene recovery zone to produce a lower boiling benzene containing fraction and a higher boiling fraction comprising a mixture of monoalkyl and polyalkyl benzenes;

f) recycling benzene from said benzene recovery zone through said second heat exchanger in indirect contact with said alkylated product from said alkylation reaction zone;

g) passing a first portion of said benzene from said second heat exchanger to at least one intermediate bed in said reaction zone;

h) passing a second portion of said benzene from said second heat exchanger through said first heat exchanger in indirect contact with said alkylation product to a bed of said reaction zone preceding said intermediate bed;

i) supplying said higher boiling fraction from said benzene recovery zone to a secondary separation zone;

j) operating said secondary separation zone to produce a second lower boiling fraction comprising a monoalkylated aromatic component and a higher boiling fraction comprising a heavier polyalkylated aromatic component;

k) supplying benzene and at least a portion of said polyalkylated aromatic component including substantially all of the dialkyl and trialkyl benzene in said polyalkylated product through a third heat exchanger connected in parallel with said first heat exchanger to a transalkylation reaction zone containing a zeolite transalkylation catalyst;

l) operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content; and m) supplying at least a portion of said disproportionation product to said benzene recovery zone.

2. In an alkylation/transalkylation process, the steps comprising:

a) supplying a feedstock containing benzene to a multi-stage alkylation reaction zone having a plurality of serially connected catalyst beds, comprising an initial bed and at least one following bed, which are operated at different temperatures;

b) supplying a $C_2$–$C_4$ alkylating agent to said reaction zone;

c) operating said reaction zone at temperature and pressure conditions to maintain said benzene in the gaseous phase and cause gas-phase alkylation of said benzene by said alkylating agent in said catalyst beds to produce an alkylated product comprising alkyl benzene and polyalkyl benzene;

d) recovering said alkylated product from said reaction zone and supplying at least a portion of said product from said reaction zone in parallel through a first heat exchanger and a second heat exchanger and then through a third heat exchanger serially following said first and second heat exchangers to a benzene recovery zone for the separation of benzene from alkylation product;

e) operating said benzene recovery zone to produce a lower boiling benzene containing fraction and a higher boiling fraction comprising a mixture of monoalkyl and polyalkyl benzenes;

f) recycling benzene from said benzene recovery zone through one of said heat exchangers in indirect contact with said alkylated product from said alkylation reaction zone;

g) passing a first portion of said benzene from said one of said heat exchangers to said reaction zone;

h) passing a second portion of said benzene from said one of said heat exchangers through another of said heat exchangers in indirect contact with said alkylated product to said reaction zone;

i) supplying said higher boiling fraction from said benzene recovery zone to a secondary separation zone;

j) operating said secondary separation zone to produce a second lower boiling fraction comprising a monoalkylated aromatic component and a higher boiling fraction comprising a heavier polyalkylated aromatic component;

k) supplying benzene and at least a portion of said polyalkylated aromatic component including substantially all of the dialkyl and trialkyl benzene in said polyalkylated product through the remaining of said heat exchangers in indirect contact with said alkylated product to a transalkylation reaction zone;

l) operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content; and m) supplying at least a portion of said disproportionation product to said benzene recovery zone.

3. The alkylation/transalkylation process of claim 2, wherein:

in step f) said one of said heat exchangers is said third heat exchanger;

in step g) said one of said heat exchangers is said third heat exchanger;

in step g) said first portion of said benzene is passed from said one of said heat exchangers to said at least one following bed in said reaction zone;

in step h) said one of said heat exchangers is said third heat exchanger;

in step h) said another of said heat exchangers is said first heat exchanger;

in step h) said second portion of said benzene is recycled to a bed of said reaction zone preceding said following bed receiving said first portion of said benzene from said one of said heat exchangers;

in step k) said remaining of said heat exchangers is said second heat exchanger;

in step k) said transalkylation reaction zone contains a zeolite transalkylation catalyst.

4. The alkylation/transalkylation process of claim 2, wherein:

in step g) said first portion of said benzene is passed from said one of said heat exchangers to said at least one following bed in said reaction zone;

in step h) said second portion of said benzene is recycled to a bed of said reaction zone preceding said following bed receiving said first portion of said benzene from said one of said heat exchangers.

5. The alkylation/transalkylation process of claim 2 wherein in step h) said bed of said reaction zone preceding said following bed receiving said first portion of said benzene from said one of said heat exchangers is said initial bed of said reaction zone.

6. The alkylation/transalkylation process of claim 2, wherein:

in step f) said one of said heat exchangers is said third heat exchanger;

in step g) said one of said heat exchangers is said third heat exchanger;

in step h) said one of said heat exchangers is said third heat exchanger;

in step h) said another of said heat exchangers is said first heat exchanger;

in step k) said remaining of said heat exchangers is said second heat exchanger.

7. The alkylation/transalkylation process of claim 2, wherein:

in step k) said transalkylation reaction zone contains a zeolite transalkylation catalyst.

8. The alkylation/transalkylation process of claim 2, wherein:

in step e) said benzene recovery zone is operated in a first and second stage, each stage producing a lower boiling fraction containing primarily benzene and a higher boiling fraction comprising a mixture of monoalkyl and polyalkyl benzenes.

9. The alkylation/transalkylation process of claim 8, wherein in step f) said benzene recycled from said benzene recovery zone through one of said heat exchangers is from said first stage of said benzene recovery zone;

and comprising the additional step f1), in between step f) and step g), of recycling at least a portion of benzene from said second stage of said benzene recovery zone through said one of said heat exchangers in indirect contact with said alkylated product from said alkylation reaction zone.

10. The alkylation/transalkylation process of claim 8 wherein in step m) said portion of said disproportionation product is supplied to said first stage of said benzene recovery zone.

11. The alkylation/transalkylation process of claim 2, wherein:

in step f) said benzene recycled from said benzene recovery zone through said one of said heat exchangers constitutes a first portion of said benzene from said benzene recovery zone;

in step h) said second portion of said benzene from said one of said heat exchangers is passed serially through said another of said heat exchangers and through a reactor feed heater to said reaction zone;

and comprising the additional step h1), between step h) and step i), of recycling a second portion of benzene from said benzene recovery zone through a separate coil in said reactor feed heater to said reaction zone.

12. In an alkylation/transalkylation process, the steps comprising:

a) supplying a feedstock containing benzene to a multistage alkylation reaction zone having a plurality of serially connected catalyst beds, comprising an initial bed and at least one following bed, which are operated at different temperatures;

b) supplying a $C_2$–$C_4$ alkylating agent to said reaction zone;

c) operating said reaction zone at temperature and pressure conditions to maintain said benzene in the gaseous phase and cause gas-phase alkylation of said benzene by said alkylating agent in said catalyst beds to produce an alkylated product comprising alkyl benzene and polyalkyl benzene;

d) recovering said alkylated product from said reaction zone and supplying at least a portion of said product from said reaction zone through a first heat exchanger, a second heat exchanger, and a third heat exchanger to a benzene recovery zone for the separation of benzene from alkylation product;

e) operating said benzene recovery zone to produce a lower boiling fraction containing primarily benzene and a higher boiling fraction comprising a mixture of monoalkyl and polyalkyl benzenes;

f) recycling benzene from said benzene recovery zone through one of said heat exchangers in indirect contact with said alkylated product from said alkylation reaction zone;

g) passing a first portion of said benzene from said one of said heat exchangers to said reaction zone;

h) passing a second portion of said benzene from said one of said heat exchangers to said reaction zone;

i) supplying said higher boiling fraction from said benzene recovery zone to a secondary separation zone;

j) operating said secondary separation zone to produce a second lower boiling fraction comprising a monoalkylated aromatic component and a higher boiling fraction comprising a heavier polyalkylated aromatic component;

k) supplying benzene and at least a portion of said polyalkylated aromatic component including substantially all of the dialkyl and trialkyl benzene in said polyalkylated product through another of said heat exchangers in indirect contact with said alkylated product to a transalkylation reaction zone;

l) operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content;

m) supplying at least a portion of said disproportionation product through the remaining of said heat exchangers in indirect contact with said alkylated product to a flash vessel;

n) operating said flash vessel to produce a lower boiling fraction of said disproportionation product containing primarily benzene and a higher boiling fraction of said disproportionation product comprising a mixture of monoalkyl and polyalkyl benzenes;

o) supplying said lower boiling fraction of said disproportionation product to said benzene recovery zone;

p) supplying said higher boiling fraction of said disproportionation product to said benzene recovery zone.

13. The alkylation/transalkylation process of claim 12, wherein:
in step d) said portion of said product from said reaction zone travels serially through said first, second, and third heat exchangers.

14. The alkylation/transalkylation process of claim 12, wherein:
in step g) said first portion of said benzene is passed from said one of said heat exchangers to said at least one following bed in said reaction zone;
in step h) said second portion of said benzene is recycled to a bed of said reaction zone preceding said following bed receiving said first portion of said benzene from said one of said heat exchangers.

15. The alkylation/transalkylation process of claim 14, wherein:
in step h) said bed of said reaction zone preceding said following bed receiving said first portion of said benzene from said one of said heat exchangers is said initial bed of said reaction zone.

16. The alkylation/transalkylation process of claim 12, wherein:
in step e) said benzene recovery zone is operated in a first and second stage, each stage producing a lower boiling fraction containing primarily benzene and a higher boiling fraction comprising a mixture of monoalkyl and polyalkyl benzenes.

17. The alkylation/transalkylation process of claim 16, wherein in step f) said benzene recycled from said benzene recovery zone through one of said heat exchangers is from said first stage of said benzene recovery zone;
and comprising the additional step f1), in between step f) and step g), of recycling at least a portion of benzene from said second stage of said benzene recovery zone through said one of said heat exchangers in indirect contact with said alkylated product from said alkylation reaction zone.

18. The alkylation/transalkylation process of claim 12, wherein:
in step f) said one of said heat exchangers is said third heat exchanger;
in step g) said one of said heat exchangers is said third heat exchanger;
in step h) said one of said heat exchangers is said third heat exchanger;
in step k) said another of said heat exchangers is said second heat exchanger;
in step m) said remaining of said heat exchangers is said first heat exchanger.

19. The alkylation/transalkylation process of claim 12, wherein:
in step k) said transalkylation reaction zone contains a zeolite transalkylation catalyst.

20. The alkylation/transalkylation process of claim 12, wherein:
in step o) said lower boiling fraction of said disproportionation product to is supplied to said first stage of said benzene recovery zone;
in step p) said higher boiling fraction of said disproportionation product is supplied to said second stage of said benzene recovery zone.

21. The alkylation/transalkylation process of claim 12, wherein:

in step f) said benzene recycled from said benzene recovery zone through said one of said heat exchangers constitutes a first portion of said benzene from said benzene recovery zone;
in step h) said second portion of said benzene from said one of said heat exchangers is passed through a reactor feed heater on the way to said reaction zone;
and comprising the additional step h1), between step h) and step i), of recycling a second portion of benzene from said benzene recovery zone through a separate coil in said reactor feed heater to said reaction zone.

22. In an alkylation/transalkylation process, the steps comprising:
a. supplying a feedstock containing benzene to a multistage alkylation reaction zone having a plurality of serially connected catalyst beds, comprising an initial bed and at least one following bed, which are operated at different temperatures;
b. supplying a $C_2$–$C_4$ alkylating agent to said reaction zone;
c. operating said reaction zone at temperature and pressure conditions to maintain said benzene in the gaseous phase and cause gas-phase alkylation of said benzene by said alkylating agent in said catalyst beds to produce an alkylated product comprising alkyl benzene and polyalkyl benzene;
d. recovering said alkylated product from said reaction zone and supplying at least a portion of said product from said reaction zone through one heat exchanger and another heat exchanger serially following said one heat exchanger to a benzene recovery zone for the separation of benzene from alkylation product;
e. operating said benzene recovery zone to produce a lower boiling benzene containing fraction and a higher boiling fraction comprising a mixture of monoalkyl and polyalkyl benzenes;
f. recycling benzene from said benzene recovery zone through one of said heat exchangers in indirect contact with said alkylated product from said alkylation reaction zone;
g. passing a first portion of said benzene from said one of said heat exchangers to said reaction zone;
h. passing a second portion of said benzene from said one of said heat exchangers to said reaction zone;
i. supplying said higher boiling fraction from said benzene recovery zone to a secondary separation zone;
j. operating said secondary separation zone to produce a second lower boiling fraction comprising a monoalkylated aromatic component and a higher boiling fraction comprising a heavier polyalkylated aromatic component;
k. supplying benzene and at least a portion of said polyalkylated aromatic component including substantially all of the dialkyl and trialkyl benzene in said polyalkylated product through the remaining of said heat exchangers in indirect contact with said alkylated product to a transalkylation reaction zone;
l. operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content; and
m. supplying at least a portion of said disproportionation product to said benzene recovery zone.

23. The alkylation/transalkylation process of claim 22, wherein:
- in step f) said one of said heat exchangers is said another heat exchanger;
- in step g) said one of said heat exchangers is said another heat exchanger;
- in step g) said first portion of said benzene is passed from said one of said heat exchangers to said at least one following bed in said reaction zone;
- in step h) said one of said heat exchangers is said another heat exchanger;
- in step h) said second portion of said benzene is recycled to a bed of said reaction zone preceding said following bed receiving said first portion of said benzene from said one of said heat exchangers;
- in step k) said remaining of said heat exchangers is said one heat exchanger;
- in step k) said transalkylation reaction zone contains a zeolite transalkylation catalyst.

24. The alkylation/transalkylation process of claim 22, wherein:
- in step g) said first portion of said benzene is passed from said one of said heat exchangers to said at least one following bed in said reaction zone;
- in step h) said second portion of said benzene is recycled to a bed of said reaction zone preceding said following bed receiving said first portion of said benzene from said one of said heat exchangers.

25. The alkylation/transalkylation process of claim 22 wherein in step h) said bed of said reaction zone preceding said following bed receiving said first portion of said benzene from said one of said heat exchangers is said initial bed of said reaction zone.

26. The alkylation/transalkylation process of claim 22, wherein:
- in step f) said one of said heat exchangers is said another heat exchanger;
- in step g) said one of said heat exchangers is said another heat exchanger;
- in step h) said one of said heat exchangers is said another heat exchanger;
- in step k) said remaining of said heat exchangers is said one heat exchanger.

27. The alkylation/transalkylation process of claim 22, wherein:
- in step k) said transalkylation reaction zone contains a zeolite transalkylation catalyst.

28. The alkylation/transalkylation process of claim 22, wherein:
- in step e) said benzene recovery zone is operated in a first and second stage, each stage producing a lower boiling fraction containing primarily benzene and a higher boiling fraction comprising a mixture of monoalkyl and polyalkyl benzenes.

29. The alkylation/transalkylation process of claim 28, wherein in step f) said benzene recycled from said benzene recovery zone through one of said heat exchangers is from said first stage of said benzene recovery zone;
- and comprising the additional step f1), in between step f) and step g), of recycling at least a portion of benzene from said second stage of said benzene recovery zone through said one of said heat exchangers in indirect contact with said alkylated product from said alkylation reaction zone.

30. The alkylation/transalkylation process of claim 28 wherein in step m) said portion of said disproportionation product is supplied to said first stage of said benzene recovery zone.

31. The alkylation/transalkylation process of claim 22, wherein:
- in step f) said benzene recycled from said benzene recovery zone through said one of said heat exchangers constitutes a first portion of said benzene from said benzene recovery zone;
- in step h) said second portion of said benzene from said one of said heat exchangers is passed through a reactor feed heater to said reaction zone;
- and comprising the additional step h1), between step h) and step i), of recycling a second portion of benzene from said benzene recovery zone through a separate coil in said reactor feed heater to said reaction zone.

* * * * *